United States Patent [19]

Shanker et al.

[11] 4,112,953

[45] Sep. 12, 1978

[54] PACER STIMULATOR WITH IMPROVED LEAD CONNECTOR

[75] Inventors: Irvin Paul Shanker, Huntingdon Valley; Teodozij Tryciecky, Philadelphia, both of Pa.

[73] Assignee: Medcor, Inc., Hollywood, Fla.

[21] Appl. No.: 776,567

[22] Filed: Mar. 11, 1977

[51] Int. Cl.² .............................................. A61N 1/36
[52] U.S. Cl. ............................. 128/419 P; 339/256 R
[58] Field of Search ................. 128/419 P; 339/64 R, 339/67, 70, 95 A, 95 R, 199 C, 199 R, 215 S, 221 R, 250, 251, 252 R, 255 R, 256 R, 262 R

[56] References Cited

U.S. PATENT DOCUMENTS

| | | | |
|---|---|---|---|
| 3,107,966 | 10/1963 | Bonhomme | 339/256 R X |
| 3,908,668 | 9/1975 | Bolpuc | 128/419 P |
| 4,027,678 | 6/1977 | van Oostveen et al. | 128/419 P |

*Primary Examiner*—William E. Kamm
*Attorney, Agent, or Firm*—Gary V. Pack; Anthony J. Rossi; Gilbert W. Rudman

[57] ABSTRACT

A pacemaker pulse generator for providing impulses to stimulate living tissue by means of an electrode at the distal end of a conductive catheter. The catheter is coupled to the pacemaker by means of a connector having engaging surfaces formed by a number of helically-extending, tensioned metal strands.

5 Claims, 3 Drawing Figures

PACER STIMULATOR WITH IMPROVED LEAD CONNECTOR

BACKGROUND OF THE INVENTION

The present invention relates to a tissue stimulator system of the pacemaker type, and more particularly to an improved connection system for coupling a catheter to such a pulse generator.

As is well known, body-implantable electronic pacers have been developed for artificially stimulating an organ, such as a heart, to correct or modify its behavior. In the case of the heart, stimulation is accomplished by transmitting electrical impulses from an implanted cardiac pacer to an electrode disposed in an appropriate area of heart muscle tissue by means of a catheter.

Several different types of cardiac pacers have been developed, and different sorts of electrical impulses provided by the pacers in order to more appropriately respond to cardiac malfunctions. Generally speaking, most pacers are implantable and comprise a small, self-contained sealed unit including a source of electrical energy and an electronic device for producing impulses at appropriate intervals. After a preliminary check of a pacer, it is implanted by surgically creating a subcutaneous cavity into which the pacer is slipped. An electrode at one end of a catheter is surgically implanted in cardiac tissue. The other end of the catheter is extended to the pacer, and connected to it in order to complete the necessary electrical circuit.

The conventional manner of electrically coupling the catheter to the pacer is comparatively elaborate. The pacer is provided with a female conductive member having an elongate passage for receiving a male connector of the catheter. A tapped hole extends through the side of the member to the passage. In order to electrically couple the catheter and the pacer, the male catheter connector is slipped into the passage, the fit being relatively loose. A set screw is then screwed into the threaded passage by means of a small wrench, and tightly urged against the side of the catheter connector. A sealing screw, and often an "O" ring, are then introduced into the threaded hole to prevent the set screw from loosening. Often surgical cement or sealing compound is then used to secure the sealing screw. Finally, a rubber boot which is attached to the pacemaker body and surrounds the entrance of the female connector is sealed around the male catheter connector tip by tying the boot with a length of non-absorbable suture.

The type of connector thus described, and the rather elaborate procedures necessary to connect and seal the catheter to the pacer, are required both to assure good electrical contact and to seal the connector against the ingress of body fluids. While the above-described procedure and apparatus have been widely and successfully used, in practice a number of disadvantages are inherent in them. The manipulation of the extremely small screws, seals and the like which are required is time-consuming and taxing, and difficulties may be presented in correctly manipulating and assembling a number of loose parts in the manner described. Further, when round male and female connectors are used, as is commonly the case, only line contact is achieved between the elements. Finally, removal of the pacer is complicated by the need for removal of sealing compound, sealing screws, and set screws. Accordingly, it will be understood that it would be highly advantageous to provide an implantable pacer with an improved connection means which obviates some or all of the foregoing problems.

It is therefore an object of the present invention to provide an implantable pacer having an improved connector.

Another object is to provide a pacer with a frictionally-engaging contact system.

Yet another object is to eliminate the need for separable locking means in a pacer connector.

A further object of the invention is to provide an improved connector for use with an implantable electronic pacer.

SUMMARY OF THE INVENTION

Briefly stated, in accordance with one aspect of the invention the foregoing objects are achieved by providing an electronic pacer with a female connector having an elongate passage extending at least partway therethrough, and a plurality of tensioned metal strands extending helically within the passage to form an expandable aperture for receiving, and making electrical contact with, a male connector member. In a preferred embodiment the female connector is disposed in a supporting body of hardened material. The elongate passage terminates in a flared orifice to more easily receive the male connector, and a terminal member extends from the distal, closed end of the female connector. The terminal is adapted to make an electrical connection with circuitry of the pacer, and advantageously comprises protrusions which resist withdrawal of the connector from the surrounding hardened material.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawing in which:

DESCRIPTION OF A PREFERRED EMBODIMENT

Figure 1:
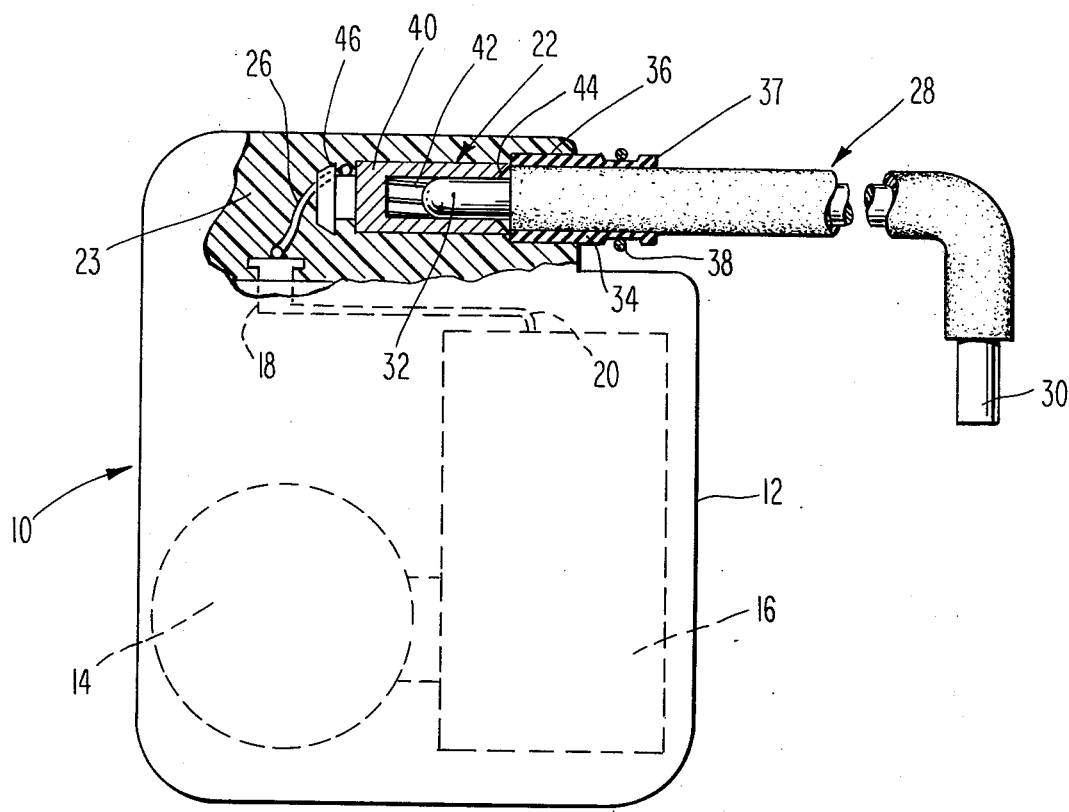
FIG. 1 is a partially cut-away view of an implantable pacer assembly.

FIG. 1 represents a self-contained implantable pacer 10 and comprises an outer envelope 12 which encloses a source of electrical energy such as battery 14, and a pulse generator 16. Typically, envelope 12 is formed of a corrosion-resistant metal such as titanium which is hermetically sealed after the batteries, circuitry and appropriate leads are disposed within the envelope. A feed-through terminal 18 extends through the uppermost wall of envelope 12 in order to conduct impulses from pulse generator 16 to a desired location. Inasmuch as the outer surface of envelope 12 often constitutes one electrode of the system, feed-through terminal 18 must be electrically insulated from the envelope. Further, it is desirable that the feed-through terminal and surrounding envelope be tightly sealed to prevent the ingress of body fluids to the interior of the envelope. An appropriate lead or the like 20 extends from the pulse generator to feed-through terminal 18 to allow electrical impulses produced by the generator to be brought out from the interior of the envelope.

A female connector generally denominated 22 is associated with the pacer, and in a presently preferred embodiment is surrounded by a mass of hardenable material 23 such as epoxy. It has been found advantageous to encapsulate the connector assembly in the manner shown both to firmly support the connector adjacent envelope 12, and to provide a fluid-tight enclosure for the system. A lead 26 extends from the feed-through terminal 18 to the connector to allow impulses provided by pulse generator 16 to be brought out from the system. Lead 26 may be welded or otherwise permanently affixed to the feed-through terminal and connector 22.

A catheter generally indicated at 28 is provided, and has at its distal end an electrode 30 which is adapted to be implanted directly into cardiac tissue. The sheath of the catheter is of non-conductive material, such as silicone rubber, and electrode 30 is advantageously of a non-corroding metal so that it will not deteriorate when implanted in tissue.

At the proximal end of the catheter a male connector 32 is provided, and extends outwardly of the surrounding sheathing material to penetrate within female connector 22.

A boot 34 of silicone rubber is firmly attached in a counterbore 36 in the body of the epoxy potting compound. Preferably, surgical adhesive is used to attach the boot firmly to the surrounding epoxy. The boot terminates in a flange section 37, the reduced-diameter neck between the flange and the body of the boot providing a convenient site for an encircling member such as ligature 38. When the catheter lead is urged through boot 34 and into close connection with the pacer elements, the rubber boot tightly grips the surface of the catheter lead, providing a fluid-tight seal which prevents body fluids from entering. After the catheter end 32 is seated within connector 22, an encircling member 38 is tied tightly about the boot in order to more firmly lock the catheter lead into position.

An important feature of the present invention is the configuration of the female connector 22. The connector comprises a rigid, elongate body 40 formed generally in the shape of a sleeve, to define an elongate passage for receiving male connector 32. Extending generally helically within the passage are a plurality of metal strands 42 which surround and engage male connector 32. A connector having a similar internal configuration, and marketed under the trademark "Hypertac," is manufactured by The Hypertronics Corp. of Stow, Mass. With this type of connector, a rigid, cylindrical form is provided and a series of metal wires are strung in tension within the cylinder. Inasmuch as the wires are strung generally helically, and in tension, they define a hyperbolic surface and moreover form a resilient aperture within the ends of the connector. Upon insertion of a male member therein, the wires are urged radially outwardly, and grip the penetrating member along a plurality of generally helical loci.

The connector of the present invention is provided with a flaring orifice 44 at the open end thereof, as the present inventors have found that this enhances entry of the positive connector into the interior of the female connector. Still further, a terminal 46 is integrally formed with the body of the female connector, and extends outwardly therefrom both to form a convenient site for attaching lead 26 and to securely anchor the connector within the surrounding mass of hardenable material 23.

Figure 2:
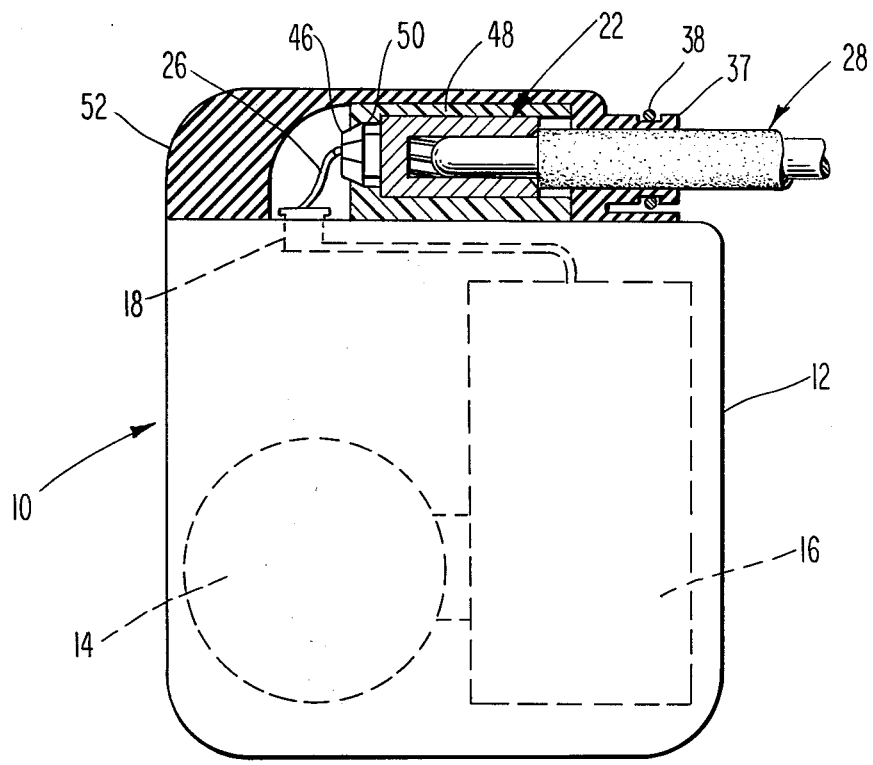
FIG. 2 illustrates another embodiment of the invention.

FIG. 2 illustrates an embodiment similar to FIG. 1, wherein an implantable pacer 10 including an envelope 12, battery 14 and pulse generator 16 has connected thereto a catheter 28 by way of connector 22. Rather than being encapsulated in a monolithic block of epoxy, however, a preformed support block 48 is provided. As shown, block 48 is provided with an axially-extending bore exhibiting a first, major diameter and a second, minor diameter. The minor diameter, illustrated at the leftward end of the block, receives the terminal end 46 of connector 22. The diameter of the smaller bore is somewhat less than the diameter of barbs or edges 50 of the terminal end of the connector, so that the latter can be forced into the smaller bore and lodge there. The configuration of the protruding barbs 50 resists withdrawal of the connector from the surrounding plastic.

In one successfully-tested embodiment the plastic block 48 was formed of nylon. However, it should be apparent that many other types of moderately resilient, plastic materials will do as well. The plastic block is secured to the lower body of the pacer by appropriate means, such as a dovetail or bayonet fitting which can be peened or upset to permanently secure the plastic block in place.

As before, a conductive lead 26 is secured, as by welding or soldering, from a feed-through terminal 18 to terminal 46 of the connector. In order to fully enclose the connector, terminals and upper part of the pacer a single all-encompassing boot 52 is provided. The latter, which may be formed from white silicone rubber, is secured to the upper surface of the pacer body by means of a surgical adhesive. The rightward end of the boot terminates in a sleeve which snugly receives the outer covering of catheter 28, and is provided with a flange 37 and tied with a non-absorbable ligature 38, as was the case with the embodiment of FIG. 1.

With the embodiment of FIG. 2, the block which retains the connector can be pre-manufactured, and the connector assembled to it before the subsequent assembly of the combination to the body of the pacer. Lead 26 may thereafter be attached, and finally boot 52 fitted over the assembly and cemented in place. In addition to ease of manufacture, the provision of an integral boot eliminates any potential problems of sealing resilient sleeve 36 within the encapsulated body 23 of the embodiment previously described.

Figure 3:
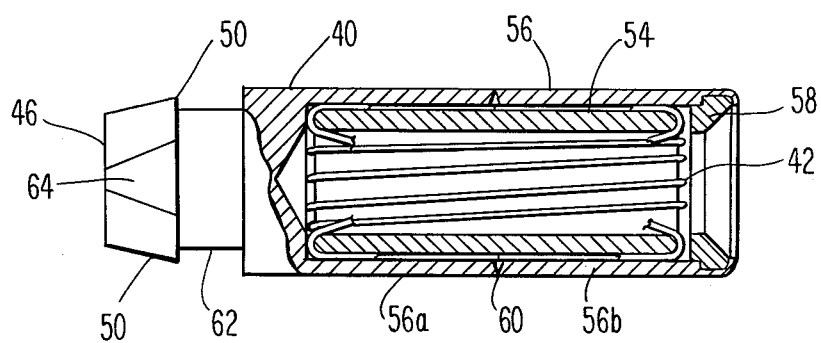
FIG. 3 is an illustration of an improved female connector suitable for use with the pacer of FIGS. 1 and 2.

Turning now to FIG. 3, there is shown in detailed form one embodiment of a connector constructed according to the present invention for use in connection with an electronic pacer. The rigid, elongate body of the female connector shown comprises a cylindrical inner sleeve 54, which may simply be a length of metal tube. The outer member of the rigid body comprises a cylindrical shell 56 having a bore opening at one end thereof and receiving sleeve 54 therewithin. The rightward, open end of member 56 is counterbored to provide a step for receiving a flared ring 58, and crimped over the latter to retain it firmly in place.

In a preferred embodiment outer shell 56 is formed of two coaxial members $56_a$ and $56_b$. The members abut at a joint 60 located at approximately midway along the length of sleeve 54. Due to this construction the ends of strands 42 which wrap about the leftward end of sleeve 54 can be placed as shown, and the sleeve forced into the leftward half of the shell. The tight fit afforded by the bore of the shell effectively locks the strands between the outer periphery of sleeve 54, and the inner surface of shell 56$_a$. The unattached ends of the strands can then be bent over the rightward end of sleeve 54, and shell 56$_b$ forced over the sleeve to abut shell 56$_a$. The latter operation serves to lock the strands in place, holding them securely during subsequent usage.

Ring 58 serves both as a retainer for sleeve 54, and as an adapter for facilitating the entry of male connector 32. In a preferred embodiment ring 58 defines a circular bore which aligns with the inner bore of sleeve 54, and further a tapered or flared outer bore, substantially as shown. The open end of outer shell 56 is crimped about ring 58, to terminate at or near the major diameter of the flared bore. At the opposite or closed end of shell 56 a terminal 46 extends to provide an abutment to which a lead may be fixed for conducting electrical impulses to the connector. The blind end of the passageway within outer shell 56 serves as a stop for locating the mating end of inner sleeve 54. The relatively massive, closed end of the outer shell further adds strength to the assembly, and provides support for terminal 46.

By configuring terminal 46 in the manner shown to provide generally laterally-extending protrusions or barbs 50, an anchoring or locking means is constituted which permanently locates the connector assembly within a supporting body as shown in FIGS. 1 and 2. In the embodiment illustrated in FIG. 3, the laterally-extending members 50 constitute opposite sides of a generally annular boss connected to the blind end of shell 56 by a neck section 62 of reduced diameter. As illustrated, a flat 64 may be machined upon either side of the annular abutment so that, in essence, a pair of diametrically opposed members are formed and rotation of the assembly within a supporting body is precluded.

The configuration of the terminal end of the connector assembly thus gives rise to several advantages. For one thing, it provides a shallow "groove" in which a conductor can be wrapped partway around, and fastened to, the terminal. For another, it provides an anchoring means by which the terminal assembly can be positively locked in place within surrounding material. As shown in FIG. 2, it is contemplated that pre-formed surrounding mass may be provided with an appropriate cavity and subsequently that the connector assembly may be snapped into place by forcing it into the cavity. The opposing members 50 would then be urged into a relatively small aperture and engage opposing sidewalls of the cavity to prevent dislodgement of the connector assembly.

Male connector 32 is engaged by a plurality of metal wires or strands 42 which extend from one end of inner sleeve 54 to the other. Each of the strands is bent over opposing ends of the sleeve, and fastened in place by welding or the like. Inasmuch as each strand is longitudinally stressed, i.e. in tension, it describes a straight line rather than a true helix. Accordingly, each strand subtends a short chord within the interior of sleeve 54. By providing a plurality of such strands, an aperture is defined within sleeve 54 which is substantially smaller than the inside diameter of the sleeve. The strands define a surface which may generally be described as a hyperboloid having a minimum diameter near the center of the sleeve. Due to the resiliency of the metal strands, the connector may be penetrated by a male member having a diameter substantially in excess of the aperture defined by the strands. As the male connector penetrates the strands, it separates them radially outwardly and forces them into a true helical configuration where they effectively wrap around the male connector. The resilient metal strands thus grip the male connector tightly, and further provide a plurality of line contacts about the surface of the latter.

It has been found that a pitch or angle of substantially 13.5° for the strands affords excellent retention of the male connector. Further, by forming the female connector assembly of stainless steel or a similar corrosion-resistant metal, deterioration of the metallic surface while the assembly is implanted in the body is avoided. Further, it has been found that strands formed of stainless steel perform admirably in service, exhibiting the requisite electrical and physical characteristics for mechanically gripping and transferring electrical impulses to, the mating male contact member.

It has been found that the strands grip the penetrating male connector sufficiently tightly to preclude its withdrawal under operating conditions, particularly when a catheter is fastened to a surrounding flange as shown in FIGS. 1 and 2. Equally important, with the ligature detached the male connector 32 can be inserted or withdrawn without the need for loosening or removing any portion of the female connector, and without requiring the removal of any sealing materials, cement or the like.

Accordingly, it will be understood that there has been disclosed herein a pacer unit incorporating a superior connector assembly which is not only well adapted for firm engagement in a surrounding, support structure; but also obviates the need for set screws, sealing screws, cement and the like, and moreover precludes the possibility of deformation of the male connector member by clamping means such as the set screws.

As will be evident from the foregoing description, certan aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

What is claimed as new and desired to be secured by Letters Patent of the United States is:

1. In a pacer for stimulating living tissue and including pulse generator means and a source of electrical potential for the pulse generating means, means for connecting said pulse generator to a conductive lead, comprising:
   (a) an elongate rigid body defining an elongate passage therewithin, said passage having a generally circular cross section and extending at least partway through said body;
   (b) a plurality of metal strands extending helically within said passage, said strands being longitudinally stressed to define an expandable aperture for resiliently receiving a male connector member therewithin;
   (c) said passage terminating in a flared orifice at a first end of said rigid body;
   (d) a neck member extending from a second end of said body opposite said first end and having a size smaller than said body;
   (e) a terminal member extending from the neck member and having a size larger than the neck member;
   (f) conductor means for electrically coupling said terminal member to said pulse generator means so that the pulses produced by said pulse generating means are conducted through the terminal member to the conductive lead; and, (g) a mass of hardenable non-conductive material molded about said elongate body, neck member, and said terminal member, whereby said terminal and neck member cooperate to resist withdrawal of said body from said mass of hardenable material.

2. A pacer according to claim 1, further comprising a flange means extending outwardly from the first end of said rigid body and terminating in a generally circular bead of enlarged cross section as compared to the internal cross section of said body, thereby facilitating insertion of the male connector of the conductive lead into said body.

3. A pacer according to claim 1, wherein the cross sectional shape along the longitudinal axis has a non-circular shape, thereby preventing rotation of said body within said mass of non-conductive material.

4. A pacer according to claim 3, wherein said metal strands extend at substantially 13.5° to the longitudinal axis of said elongate passage.

5. A pacer according to claim 4, wherein said metal strands are formed of stainless steel.

* * * * *